United States Patent [19]

Köch et al.

[11] Patent Number: 4,550,174
[45] Date of Patent: Oct. 29, 1985

[54] PROCESS FOR REDUCING THE PROPORTIONS OF BY PRODUCTS IN THE PREPARATION OF CARBENDAZIM

[75] Inventors: Manfred Köch, Eppstein; Thomas Maier, Frankfurt am Main, both of Fed. Rep. of Germany

[73] Assignee: Hoechst Aktiengesellschaft, Frankfurt, Fed. Rep. of Germany

[21] Appl. No.: 622,839

[22] Filed: Jun. 21, 1984

[30] Foreign Application Priority Data

Jun. 25, 1983 [DE] Fed. Rep. of Germany ....... 3323024

[51] Int. Cl.⁴ .......................................... C07D 235/32
[52] U.S. Cl. .................................................... 548/306
[58] Field of Search ......................................... 548/306

[56] References Cited

U.S. PATENT DOCUMENTS 3,897,448 7/1975 Moyne ............................... 548/306

Primary Examiner—Richard A. Schwartz
Attorney, Agent, or Firm—Curtis, Morris & Safford

[57] ABSTRACT

The invention relates to a process for the preparation of highly pure carbendazim

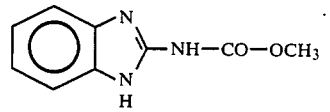

which starts from o-phenylenediamine and methyl cyanocarbamate, and, in addition, a reducing agent is added.

9 Claims, No Drawings

PROCESS FOR REDUCING THE PROPORTIONS OF BY PRODUCTS IN THE PREPARATION OF CARBENDAZIM

Carbendazim(methyl 2-benzimidazolcarbamate) of the formula

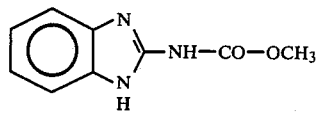

is a valuable fungicide having a broad spectrum of action (H. Martin, Pesticide Manual (1977) p. 78, British Crop Protection Council). It can be used both as an industrial fungicide and, in particular, as a plant fungicide having systemic activity.

In all current syntheses, the preparation of carbendazim is carried out using ortho-phenylenediamine as a structural unit in the synthesis. The latter is advantageously reacted with methyl cyanocarbamate in accordance with German Offenlegungsschrift No. 1,668,557 and German Offenlegungsschrift No. 1,795,849, the methyl cyanocarbamate being used either directly in the solution from its synthesis, without isolation, or after it has been isolated. In these reactions, dimeric and polymeric condensates of phenylenediamine are produced as byproducts, and these lead to undesired discoloration of the product and to effluent pollution. In addition, some of the byproducts have toxic properties.

Thus, with a view to using carbendazim as an industrial fungicide for protective coatings, it is important to eliminate the additional coloring substances. Likewise, it is important for use in agriculture that the proportion of byproducts in the carbendazim is reduced.

This object has been achieved by the present invention, surprisingly, by addition of a reducing agent during the synthesis of carbendazim.

Thus the present invention relates to a process for reducing the proportions of byproducts in the synthesis of carbendazim starting from o-phenylenediamine and methyl cyanocarbamate ($CH_3O-CO-NH-CN$) in the presence of water and protonic acid, which comprises addition of a reducing agent to the reaction mixture. In this context, particularly suitable synthetic processes for the preparation of carbendazim are the processes described in the abovementioned German Offenlegungsschriften. However, it is also possible for other known synthetic processes to be used, and, according to the invention, reducing agents are added to them.

Suitable reducing agents according to the present invention are customary reducing agents, such as salts of metals in low oxidation states, for example Cu(I) halides, compounds of non-metals in low oxidation states, such as compounds of sulfur, nitrogen or phosphorus, which have reducing properties, or organic compounds which are known as reducing agents, such as phloroglucinol or formic acid.

In this context, care has to be taken that the reducing agent selected is such as does not take part in any reaction with the reactants used for the preparation of carbendazim; in particular, the oxidized form of the reducing agent should not function as an oxidizing agent or catalyst for oxidation of o-phenylenediamine. In addition, the reducing agent must have adequate stability in aqueous solution.

Particularly suitable reducing agents are compounds of sulfur containing sulfur in oxidation states below +5. These particularly include inorganic sulfur compounds, preferably polysulfides, such as alkali metal disulfides, sulfides, such as alkali metal or alkaline earth metal sulfides, hydrogensulfides, such as alkali metal or alkaline earth metal hydrogensulfides, salts of thiosulfuric acid, for example alkaline earth metal or alkali metal salts, such as $Na_2S_2O_3$, or salts of dithionous acid, for example alkaline earth metal or alkali metal salts, such as $Na_2S_2O_4$.

The amount of reducing agent used is not crucial and is advantageously less than 10% by weight relative to o-phenylenediamine employed, or less than 1% by weight relative to the total weight of the reaction mixture. As a rule, the proportion of the reducing agent is between 0.1 and 10% by weight, preferably between 0.5 and 5% by weight, relative to o-phenylenediamine, or between 0.01 and 1% by weight, preferably between 0.05 and 0.5% by weight, relative to the total reaction mixture.

The reducing agent is advantageously initially introduced with the methyl cyanocarbamate, and the reactant o-phenylenediamine is then added.

However, it is also possible for the reducing agent to be mixed in together with o-phenylenediamine or immediately after addition of the o-phenylenediamine. Delayed addition of the reducing agent diminishes the desired reduction of the proportions of byproducts.

Furthermore, it is advantageous to carry out the process under an atmosphere of inert gas, for example under nitrogen, in order to prevent the interfering effects of oxygen on the reaction.

The other reaction parameters, such as temperature and pH, are advantageously controlled as described in German Offenelgungsschrift No. 1,795,848: reaction temperature 40°–130° C.; pH of the reaction mixture 2.5 to 4.5. Aqueous hydrochloric acid is advantageously used as the protonic acid.

The process according to the invention is illustrated below by means of an example.

EXAMPLE 0.9 g of sodium dithionite was added to an aqueous solution of crude methyl cyanocarbamate (prepared from 25 g of cyanamide, 57 g of methyl chloroformate and sodium hydroxide solution under nitrogen) under an atmosphere of nitrogen at 25°–35° C., the mixture was stirred for 10 min, and 56.7 g of o-phenylenediamine were added. The mixture was heated to 70° C., and 89 ml of 32% strength hydrochloric acid was added dropwise in such a manner that a temperature range of 90°–95° and a pH of 4 were attained. After a reaction time of 3 hours at this temperature with a constant pH of 4, the precipitated product was filtered off at 70° C. The product was washed with hot water until free of chloride and then dried in vacuo. 91.6 g of highly pure methyl 2-benzimidazolcarbamate, melting point 315–318 (decomposition) were obtained; yield based on o-phenylenediamine; 91.5%.

The product is white and contains no additional coloring substances.

The purity of the product in respect of dimers and polymers of o-phenylenediamine can be characterized by means of the content of 2,3-diaminophenazine, a dimer of o-phenylenediamine. Thus, the methyl 2-benzimidazolecarbamate isolated above now contains only 0.8–0.9 ppm of 2,3-diaminophenazine. The filtrate contains only 1 to 4 ppm of 2,3-diaminophenazine and is colored only pale yellow.

We claim:

1. A process for reducing the proportions of by-products in the synthesis of carbendazim of the formula

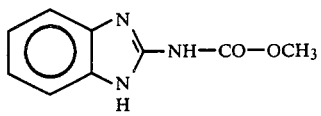

starting from o-phenylenediamine and methyl cyanocarbamate, in the presence of water and protonic acid, which comprises addition of a reducing agent to the reaction mixture.

2. The process as claimed in claim 1, wherein the reducing agent is initially introduced together with the methyl cyanocarbamate, and then the o-phenylenediamine is added.

3. The process as claimed in claim 1, wherein the reducing agent used is a compound of sulfur in which the sulfur has oxidation states below +5.

4. The process as claimed in claim 3, wherein an inorganic sulfur compound is used.

5. The process as claimed in claim 1, wherein a sulfide, polysulfide, or a salt of thiosulfuric acid or of dithionous acid is used as the reducing agent.

6. The process as claimed in claim 1, wherein the reducing agent is used in an amount of 0.1–10% by weight relative to o-phenylenediamine used.

7. The process as claimed in claim 1, wherein the reducing agent is used in an amount of 0.5 to 5% by weight relative to o-phenylenediamine used.

8. The process as claimed in claim 1, wherein the reducing agent is used in an amount of 0.01 to 1.0% by weight relative to the total reaction mixture.

9. The process as claimed in claim 1, which is carried out under an atmosphere of inert gas.

* * * * *